United States Patent
Ohashi et al.

(10) Patent No.: US 7,378,201 B2
(45) Date of Patent: May 27, 2008

(54) METHOD FOR REPAIRING A PHOTOMASK, METHOD FOR INSPECTING A PHOTOMASK, METHOD FOR MANUFACTURING A PHOTOMASK, AND METHOD FOR MANUFACTURING A SEMICONDUCTOR DEVICE

(75) Inventors: Katsuki Ohashi, Yokohama (JP); Hiromu Inoue, Yokohama (JP); Akira Ono, Tokyo (JP); Hiroyuki Ikeda, Yokohama (JP)

(73) Assignee: Kabushiki Kaisha Toshiba, Kawasaki-shi (JP)

( * ) Notice: Subject to any disclaimer, the term of this patent is extended or adjusted under 35 U.S.C. 154(b) by 0 days.

(21) Appl. No.: 11/478,650

(22) Filed: Jul. 3, 2006

(65) Prior Publication Data

US 2006/0257756 A1   Nov. 16, 2006

Related U.S. Application Data

(60) Division of application No. 10/989,314, filed on Nov. 17, 2004, now Pat. No. 7,070,889, which is a division of application No. 09/870,702, filed on Jun. 1, 2001, now Pat. No. 6,849,363, which is a continuation-in-part of application No. 09/263,937, filed on Mar. 8, 1999, now abandoned, which is a continuation-in-part of application No. 09/105,031, filed on Jun. 25, 1998, now abandoned.

(30) Foreign Application Priority Data

Jun. 27, 1997 (JP) .................................. 9-171695
Jul. 16, 1998 (JP) ................................ 10-201942

(51) Int. Cl.
G03C 5/00 (2006.01)
G03F 9/00 (2006.01)
G03K 9/00 (2006.01)

(52) U.S. Cl. .................. 430/30; 430/311; 430/945; 382/144

(58) Field of Classification Search ................... 430/5, 430/30, 311, 945; 382/144
See application file for complete search history.

(56) References Cited

U.S. PATENT DOCUMENTS

| 4,579,455 A | 4/1986 | Levy et al. |
| 4,851,978 A | 7/1989 | Ichihara |
| 5,572,598 A | 11/1996 | Wihl et al. |
| 5,763,123 A | 6/1998 | Shishido et al. |
| 6,052,478 A | 4/2000 | Wihl et al. |
| 6,849,363 B2 * | 2/2005 | Ohashi et al. ................. 430/5 |
| 7,070,889 B2 * | 7/2006 | Ohashi et al. ................. 430/5 |

FOREIGN PATENT DOCUMENTS

| JP | 01-220805 | 9/1989 |
| JP | 1290276 | 11/1989 |
| JP | 03-022407 | 1/1991 |
| JP | 5-45051 | 7/1993 |
| JP | 06-294750 | 10/1994 |
| JP | 7-86647 | 9/1995 |
| JP | 2526986 | 6/1996 |
| JP | 63-173322 | 7/1998 |
| JP | 2004-110072 | 4/2004 |
| JP | 2004-157548 | 6/2004 |

OTHER PUBLICATIONS

Japanese Notification of Reasons for Rejection Mailed Aug. 21, 2007 in corresponding application JP 2003-409607.
S. Wolf and R.N. Tauber, "Silicon Processing for the VLSI Era," Lithography II: Optical Aligners and Photomasks, pp. 630-635, 2001.

* cited by examiner

*Primary Examiner*—Christopher G. Young
(74) *Attorney, Agent, or Firm*—Finnegan, Henderson, Farabow, Garrett & Dunner, L.L.P.

(57) ABSTRACT

A method for inspecting a photomask, comprising generating a laser beam, changing a phase of the laser beam to smooth the brightness distribution of the laser beam, applying the smoothed laser beam to the photomask, acquiring an image of the photomask using a sensor while the laser beam and the photomask are relatively moved, examining the image of the photomask for a defect of the mask-pattern of the photomask.

34 Claims, 13 Drawing Sheets

METHOD FOR REPAIRING A PHOTOMASK, METHOD FOR INSPECTING A PHOTOMASK, METHOD FOR MANUFACTURING A PHOTOMASK, AND METHOD FOR MANUFACTURING A SEMICONDUCTOR DEVICE

CROSS-REFERENCE TO RELATED APPLICATIONS

The present application is a division of application Ser. No. 10/989,314, filed on Nov. 17, 2004, now U.S. Pat. No. 7,070,889 which is a division of application Ser. No. 09/870,702, filed on Jun. 1, 2001, now U.S. Pat. No. 6,849,363, which is a continuation-in-part application of U.S. patent application Ser. No. 09/263,937, filed on Mar. 8,1999, now abandoned, which is a continuation-in-part application of U.S. patent application Ser. No. 09/105,031, filed on Jun. 25, 1998, now abandoned. The entire contents of these related applications are incorporated herein by reference.

This application is based upon and claims the benefit of priority from the prior Japanese Patent Applications No. 9-171695, filed Jun. 27, 1997; No. 10-178300, filed Jun. 25, 1998; and No. 10-201942, filed Jul. 16, 1998, the entire contents of all of which are incorporated herein by reference.

BACKGROUND OF THE INVENTION

The present invention relates to a method for repairing a photomask used in manufacturing a semiconductor device comprising the step of inspecting the mask-pattern of the photomask and then repairing any defects in the mask-pattern on the basis of the inspection result.

An inspecting apparatus, used during the process for manufacturing a semiconductor devise, inspects for defects in the mask-pattern of a photomask. This apparatus has an optical system for illuminating and imaging a photomask, a sensor for acquiring the image of the photomask and outputting an image signal, and an inspection portion for inspecting the mask-pattern on the basis of the outputted image signal.

As a light source used in the optical system, a mercury lamp is generally used. The mercury lamp makes it possible to illuminate the photomask by light having wavelengths from the visible range to the ultra-violet range (around 365 nm).

Recently, the minuteness and the integrated scale of mask-patterns for a photomask have increased, as the performance of a semiconductor apparatus becomes higher. This requires an apparatus for inspecting the photomask to exhibit a higher resolution so as to detect smaller defects in the mask pattern. It is necessary to shorten the wavelength of light from the optical system to realize the higher resolving power. However, conventional mercury lamps cannot provide enough illumination intensity, in the short wave range, which can be used for the inspecting apparatus. Therefore, a laser such as an ultraviolet laser is used instead of the mercury lamp.

However, when a laser beam provides a light source for the defect inspecting apparatus, interference fringes are generated from the coherency of the laser. The generation of the interference fringes causes variations in the brightness of the acquired image outputted from the sensor; therefore, in inspecting any defect, it is impossible to decide whether this "variation" is generated from a defect in the mask-pattern or from the coherence of the laser beam.

BRIEF SUMMARY OF THE INVENTION

Therefore, one object of the present invention is to solve the above-mentioned problem caused when the laser beam is used for the light source of the apparatus for inspecting a pattern-defect of a mask-pattern. Another object is to provide a pattern-defect repairing apparatus for inspecting with a higher resolving power. Another object is repairing the defect.

According to the first aspect of the present invention, there is provided a method for repairing a sample comprising:

generating a laser beam;

changing a phase of the laser beam to smooth the brightness distribution of the laser beam, and applying the laser beam to the sample;

acquiring an image of the sample with a Time Delay Integration (TDI) sensor, and outputting an image signal from the TDI sensor in accordance with relative movement of the laser beam and the sample;

detecting a defect of the mask-pattern of the sample on the basis of the image signal output from the TDI sensor;

specifying the position of the defect of the mask-pattern on the basis of the result obtaining by the detecting step; and repairing the defect of the mask pattern.

According to the second aspect of the present invention, there is provided a method for inspecting a sample, comprising:

generating a laser beam;

changing a phase of the laser beam to smooth the brightness distribution of the laser beam;

applying the smoothed laser beam to the sample;

acquiring an image of the sample using a Time Delay Integration (TDI) sensor while the laser beam and the sample are relatively moved; and examining the image of the sample for a defect of the mask-pattern of the sample.

According to the third aspect of the present invention, there is provided a method for manufacturing a sample comprising:

forming a pattern onto the sample;

generating a laser beam;

changing a phase of the laser beam to smooth the brightness distribution of the laser beam, and applying the smoothed laser beam to the sample;

acquiring an image of the sample with a TDI sensor as the laser beam and the sample are moved relatively;

acquiring a defect of the mask-pattern of the sample on the basis of the image of the sample; and when the defect of the mask-pattern is detected, specifying the position of the defect of the mask-pattern, and repairing the defect of the mask-pattern.

According to the fourth aspect of the present invention, there is provided an apparatus for inspecting a sample comprising:

an illuminating optical system for changing a phase of a laser beam to smooth the brightness distribution of the laser beam, and for applying the smoothed laser beam to the sample;

a sensor for acquiring an image of the sample as the laser beam and the, sample move relatively;

a defect examination device for examining the image of the sample for a defect of the mask-pattern of the sample.

According to the fifth aspect of the present invention, there is provided a method for manufacturing a semiconductor device by using a sample after inspecting the sample, comprising:

generating a laser beam;

changing a phase of the laser beam to smooth the brightness distribution of the laser beam;

applying the smoothed laser beam to the sample;

acquiring an image of the sample using a time Delay Integration (TDI) sensor while the laser beam and the sample are relatively moved; and examining the image of the sample for a defect of the mask-pattern of the sample.

According to the sixth aspect of the present invention, there is provided a method for manufacturing a semiconductor device by using a sample after manufacturing the sample, comprising:

forming a pattern onto the sample;

generating a laser beam;

changing a phase of the laser beam to smooth the brightness distribution of the laser beam, and applying the smoothed laser beam to the sample;

acquiring an image of the sample with a TDI sensor as the laser beam and the sample are moved relatively;

acquiring a defect of the mask-pattern of the sample on the basis of the image of the sample; and when the defect of the mask-pattern is detected, specifying the position of the defect of the mask-pattern, and repairing the defect of the mask-pattern.

examining the image of the sample for a defect of the mask-pattern of the sample.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Referring to the attached drawings, first to sixth embodiments according to the present invention will now be described.

First Embodiment

Figure 1:
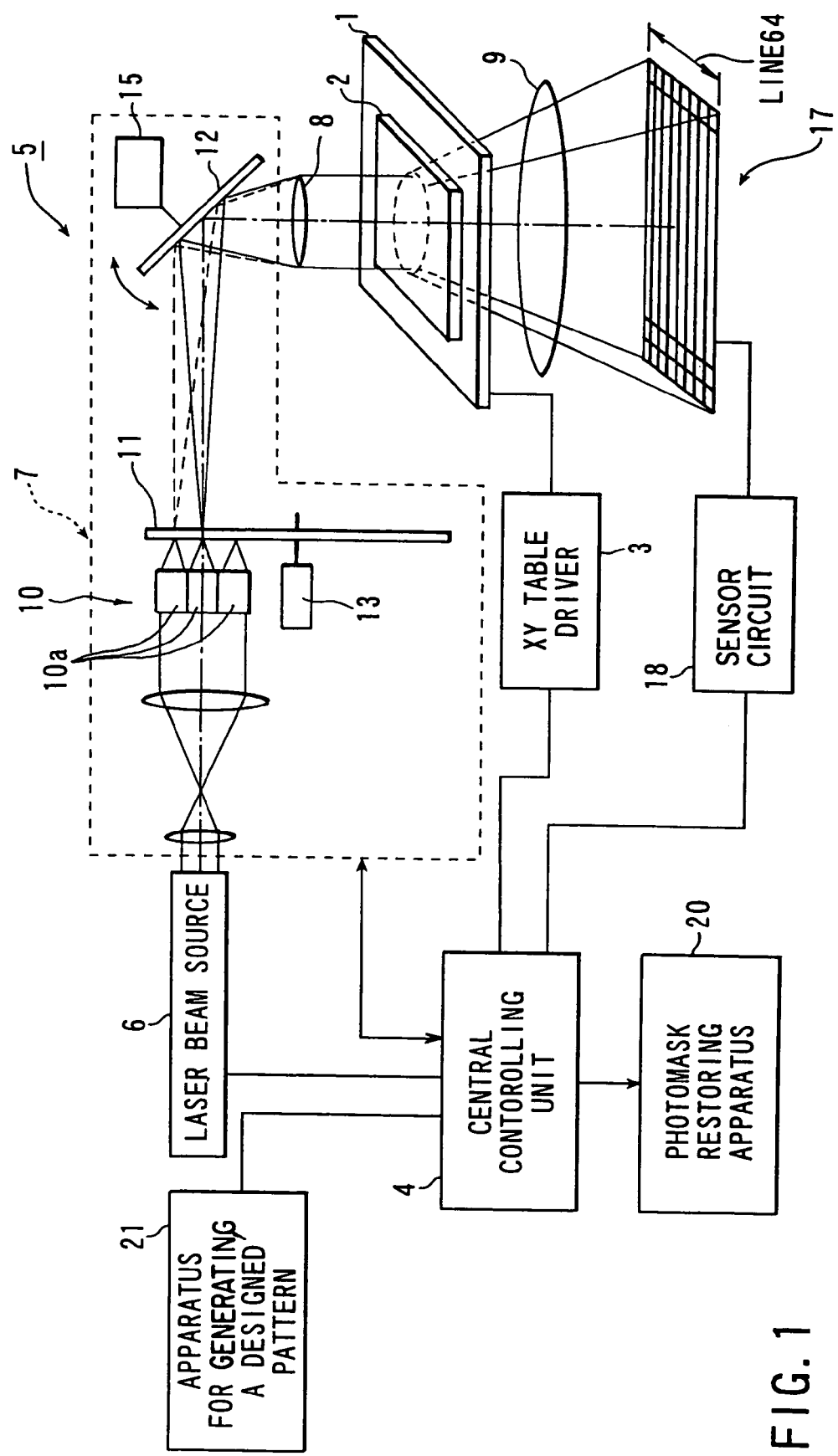
FIG. 1 is a schematic illustration of a first embodiment according to the present invention.

FIG. 1 illustrates a mask-pattern inspecting apparatus and a mask repairing apparatus 20 for repairing a mask on the basis of the results obtained from an inspection by the mask-pattern inspecting apparatus.

In FIG. 1, the reference number 1 denotes an XY table. The XY table 1 supports a sample or photomask 2, an object for inspecting and repairing, and can move the sample or photomask 2 in any XY direction. The XY table is connected to a central controlling portion 4 through a driver 3 for driving the XY table 1.

The inspecting apparatus also has an optical system 5 for illuminating the sample or photomask 2 supported by the XY table 1. The optical system 5 comprises an Ar laser 6 as a laser beam emitting source, a laser beam smoothing optical system 7 for changing interference fringes of the laser beam to make the brightness distribution of the laser beam uniform, and a condenser lens 8 for illuminating the laser beam which has passed through the laser beam smoothing optical system 7 onto the sample or photomask 2.

The laser beam smoothing optical system 7 has an integrator lens 10 (for example, a fly eye lens), a phase rotating plate 11, and a vibration mirror 12.

The fly eye lens is one of the integrator lenses and has a structure in which many lenses 10a are aligned in an array form. The fly eye lens forms secondary light source images. The pupil images of the secondary light sources overlap each other on the sample or photomask 2 to smooth the intensity distribution of the laser beam 6.

Figure 2A:
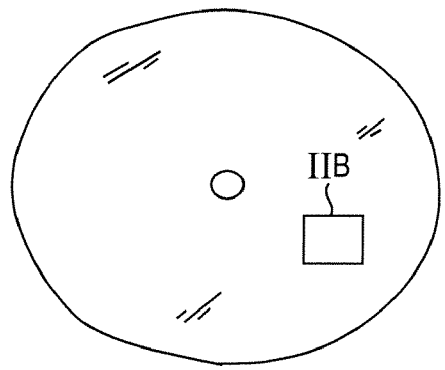
FIGS. 2A to 2C are schematic illustrations of the first embodiment, each of which shows a schematic view of a phase rotating plate.
Figure 2B:
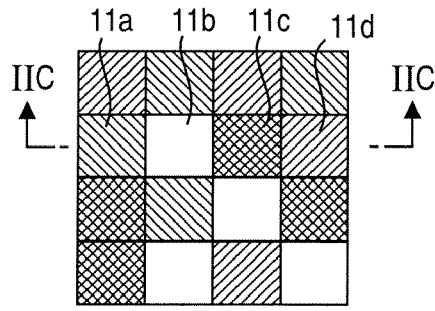
Figure 2C:
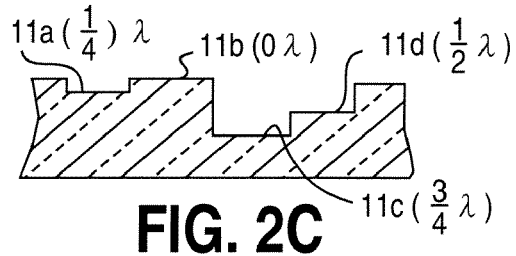

FIG. 2A shows a phase shift plate 11 which can rotate. The phase shift plate 11, illustrated in enlarged views, i.e., FIGS. 2B and 2C, is a transparent disc which consists of a large number of steps 11a to 11d. The steps 11a to 11d have different depths and are arranged at random. The phase shift plate 11 has different thickness at various points, Therefore, when the laser beam passes through the phase rotating plate 11 while the plate 11 rotates, the phase of the laser beam changes depending on the depth of the respective steps 11a to 11d. The steps 11a to 11d to have such thickness that the phase of the laser beam is shifted by 0, ¼λ, ½λ and ¾λ, respectively, where λ is the wave length of the laser beam.

A rotationally-driving motor rotationally drives the phase rotating plate 11. A motor driver, not illustrated, connects the motor 13 to a central controlling portion 4. The central controlling portion 4 controls the motor 13 so that the phase rotating plate 11 can be rotated at, for example, 10,000 rpm.

When the phase of the laser beam changes at random in such a manner as above, the interference fringes of the laser beam also change. Furthermore, carrying out this change at a high speed smoothes the brightness of the laser beam.

The vibration mirror 12 can swing and vibrate by means of a mechanically-driving unit 15 such as piezo element at, for example, 100 Hz. The mirror 12 shifts the optical axis of the laser beam reflecting from the mirror 12.

Figure 3A:
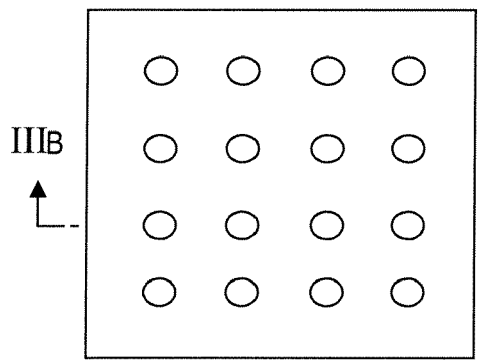
FIGS. 3A and 3B are schematic illustrations of the first embodiment, and are an image plan showing interference fringes which occurs on a sample for coherency of a laser beam, and a profile view of the wave form of brightness distribution, respectively.
Figure 3B:
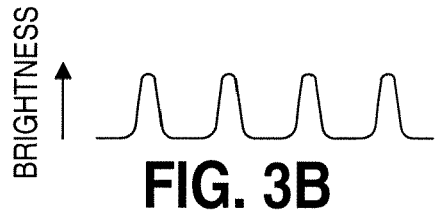
Figure 4:
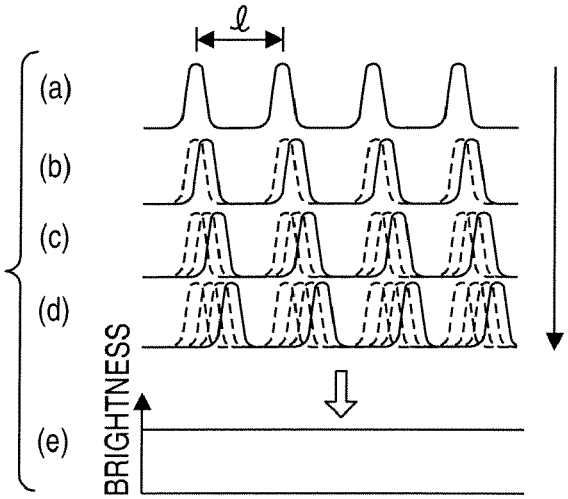
FIG. 4 is schematic illustration for explaining the first embodiment, each of which shows the process for smoothing brightness by shifting the axis of light.

Such a shift of the optical axis of the laser beam as above changes the interference fringes of the laser beam, as described in FIGS. 3A and 3B and FIG. 4. FIG. 3A is an image plan showing the brightness distribution (interference fringes) of the laser beam emitted from the laser beam source 1. FIG. 3B shows a wave profile view of the representing the brightness distribution across section IIIB-IIIB of FIG. 3A.

Vibration of the vibration mirror 12 shifts the brightness distribution wave form shown in FIG. 3B in the lateral direction, as shown in FIG. 4. When the vibration mirror 12 vibrates with such an amplitude that the width of the shift will be less than a pitch l shown in the FIG. 4, or will be in multiples of l', where l' is a value less than l, at a high speed, the brightness of the laser beam can be made uniform as illustrated in FIG. 4. The amplitude and the frequency of the vibration mirror 12 can be decided and controlled by the central controlling portion 4.

As descried above, the laser beam through the vibration mirror 12 is applied to the sample or photomask 2 through the condenser lens 8, under the condition that the brightness of the laser beam is made uniform.

Furthermore, this apparatus has a Time Delay Integration sensor 17 (TDI) shown in FIG. 1 as a sensor for acquiring the image of the sample or photomask 2. The TDI sensor comprises photoelectric elements of 64 lines, each of which has 2048 pixels and is controlled by a sensor circuit 18 shown in FIG. 1. The TDI sensor 17 integrates the photosignal storage of the lines to the neighboring line in turn. When the total intensity signals of the 64 lines are integrated, the TDI sensor outputs the result.

The integration time for the TDI sensor 17 to store the signals (the signal storing time) is identical to the time necessary for scanning the same point of the sample or photomask 2 from the 1st line to 64th line. It is preferable to set the signal storing time to a minimum time which makes it possible to smooth the brightness of the laser beam by the smoothing optical system 7.

According to the present embodiment, uniform signals which are not influenced by the coherency of the laser beam can be acquired, for example, if in the step illustrated in FIG. 4 the signal storing time becomes equal to the time required to shift the wave form of the light of the interference fringe at least one pitch l.

On the contrary, the rotation number of the phase shift plate 11 and the vibration frequency of the vibration mirror 12 may be decided so as to match the signal integration time of the storage sensor 17.

Namely, when the signal storing time of the TDI sensor 17 is short, it is necessary to smooth the brightness of the laser beam within the short time, and thus, to increase the rotation velocity of the phase rotating plate 11 and the vibration frequency of the vibration mirror 12.

In the present embodiment, uniform signals were able to be detected by rotating the phase shift plate 11 at 10,000 rpm, vibrating the vibration mirror 12 at 100 Hz, scanning one line of the storage sensor in about 30 μsec, and integrating the signal in about 30 μsec×64 (=1.92 msec).

In such a manner as above, the smoothing optical system 5 and the TDI sensor 17 illuminate the sample or photomask 2 and then detect the image generated from the illumination, thereby enabling the acquisition of the photomask or sample image without being affected by coherency. Accordingly, it becomes possible to detect the mask-pattern of the sample or photomask 2 with a high resolution.

The image of the mask-pattern detected as above is used for inspection of the mask-pattern by the central controlling portion 4, and the result obtained from the inspection is inputted into a mask repairing apparatus 20 for repairing the mask-pattern.

Figure 5:
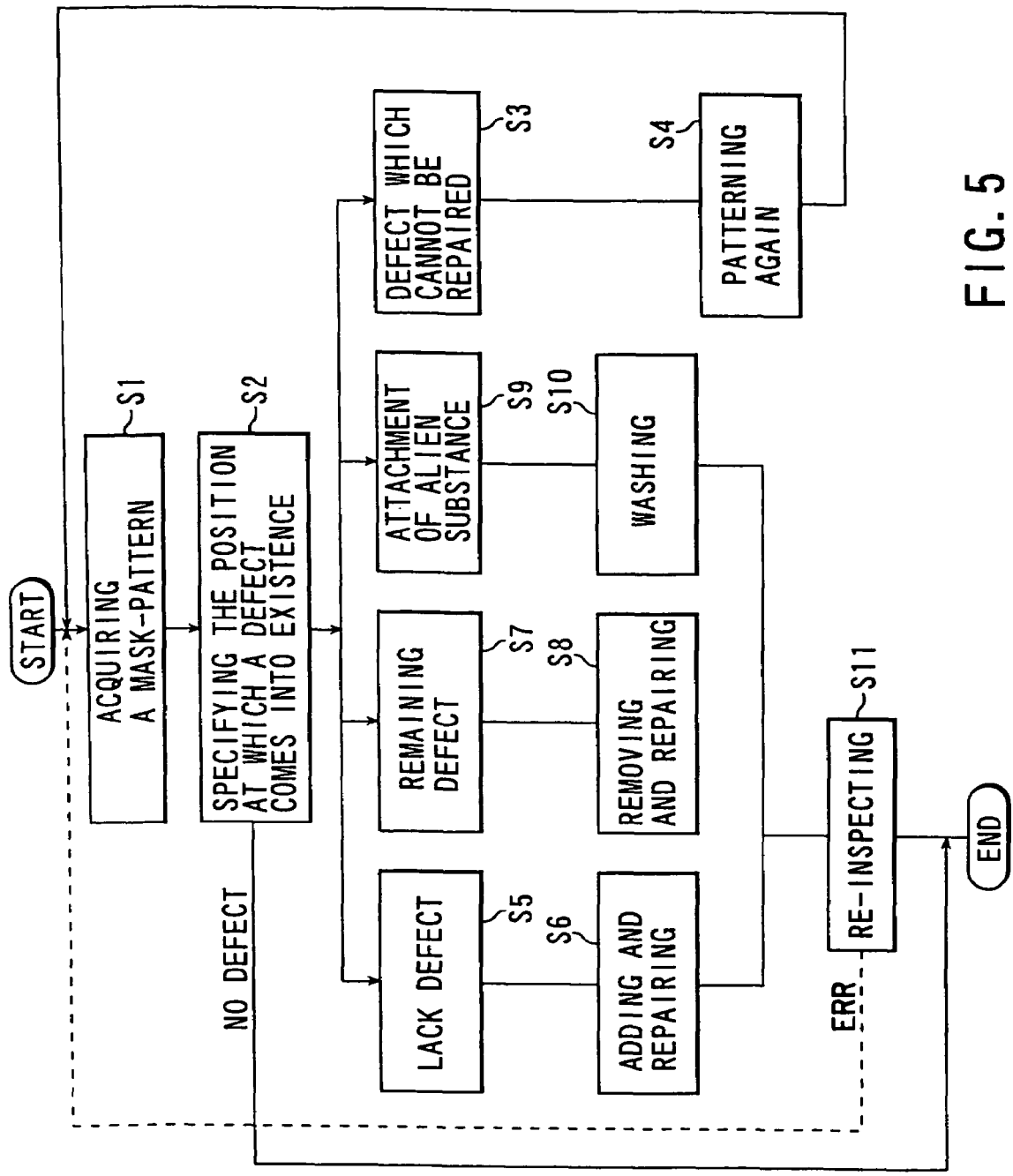
FIG. 5 is a schematic illustration of the first embodiment and is a flowchart of the process of inspecting and repairing a mask.

The steps of this inspection and repair will be described as follows, with reference to a flowchart shown in FIG. 5.

Firstly, the system determines whether the pattern is formed at a position as designed or not and whether the formed pattern has a defect or not (step S1). Potential defects include lack of a part of the pattern (intrusion), remaining of unnecessary portions to be removed off (protrusion), and attachment of a particle.

After the completion of the inspection of the mask-pattern in the step S1, the central controlling portion 4 specifies the position of each defect, and the type of the defect (step S2). In this step, either the die-comparison method or the database pattern-comparison method can be used appropriately, as a method for inspecting for a pattern defect. The former is defined as the method of inspecting for defects by comparing neighboring, identical, patterns, and the latter is defined as the method of inspecting for defects by comparing data on the designed pattern with the measured pattern.

The present embodiment adopts the designed pattern-comparison method. A designed data generating apparatus 21 is shown in FIG. 1. The inspection is performed first by matching the position between the mask-pattern images obtained from the TDI sensor 17 and the position of the designed pattern image (CAD data) generated by the designed data generating apparatus 21, and then comparing these images to detect defects with its position and the type.

When no defect is detected in the step S2, the inspection is finished (End). If a detected defect cannot be repaired, for example, when the defects are large, located across neighboring patterns or located at a corner point (step S3), the mask-pattern is removed from the photomask or sample and patterned again (step S4).

After specifying the defect position and the type of defect in the step S2, the central controlling portion 4 delivers the information to the photomask or sample repairing apparatus 20 along with the sample or photomask 2.

In the photomask or sample repairing apparatus, a suitable repairing method is carried out according to the type of defect. When the detected defect is decided to be an intrusion (step S5), a pattern is added to the defect on the basis of the information of the defect position to repair it into a normal pattern (step S6). A pattern may be added, for example, by a focused ion beam. When the defect is decided to be a protrusion (step S7), an unnecessary pattern is removed on the basis of the information of the remaining-position by means of, for example, an electronic beam or a laser beam (step 8).

When the defect is decided to be a particle (step S9), the sample or photomask 2 is delivered to a washing step (step S10) to remove the particle.

After the above-mentioned steps are carried out, the photomask or sample repairing apparatus 20 delivers the sample or photomask 2 together with the information on the defect-position to the photomask or sample inspecting apparatus shown FIG. 1.

The inspection apparatus inspects the position of the defect repairing portion of the sample or photomask 2 based on the information of the detected defect position, and inspects the acquired images according to the step S2 again. According to one embodiment, only the position of the defect is inspected. If necessary, the sample or photomask 2 is delivered to the repairing apparatus 20 again and then the repairing process of the steps S4 to 10 is carried out.

The above-mentioned apparatus and steps make it possible to obtain a photomask or sample pattern image which is not affected by coherency of a laser and, as a result, to inspect with high precision. Furthermore, a defect on a sample or photomask 2 can be repaired according to the information having high precision.

The first embodiment has the vibration mirror 12 in the smoothing optical system 7, however, similar advantages can be obtained even if the vibration mirror 12 is not provided.

Figure 6:
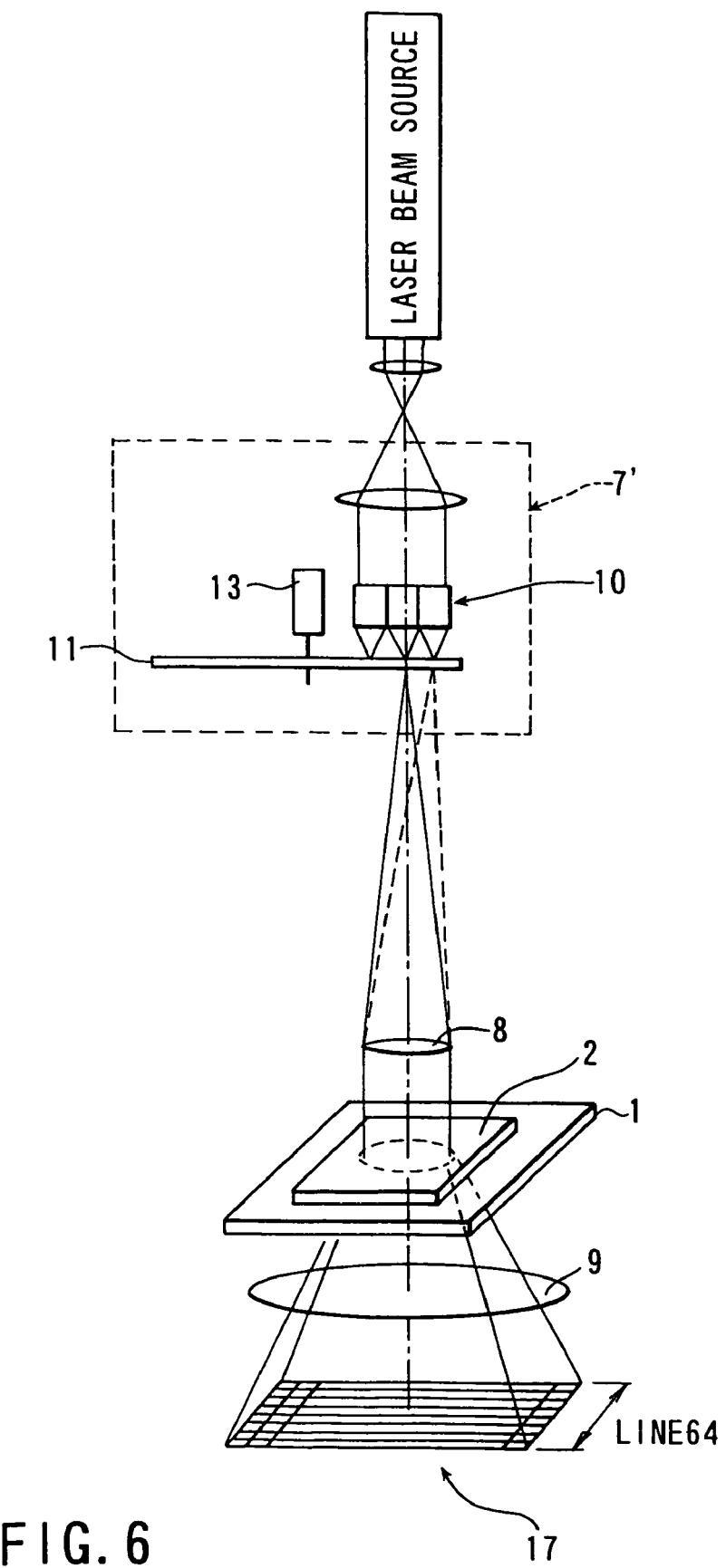
FIG. 6 is a schematic illustration of a variation of the first embodiment.

FIG. 6 illustrates another example of the first embodiment. In this embodiment, as well, the storing time of the TDI sensor 17 may be determined in accordance with the time during which the brightness of the laser beam can be made uniform by the rotation of the phase shift plate.

On the contrary, the rotation velocity of the phase shift plate may be determined in accordance with the storing time of the TDI sensor.

Second Embodiment

Figure 7:
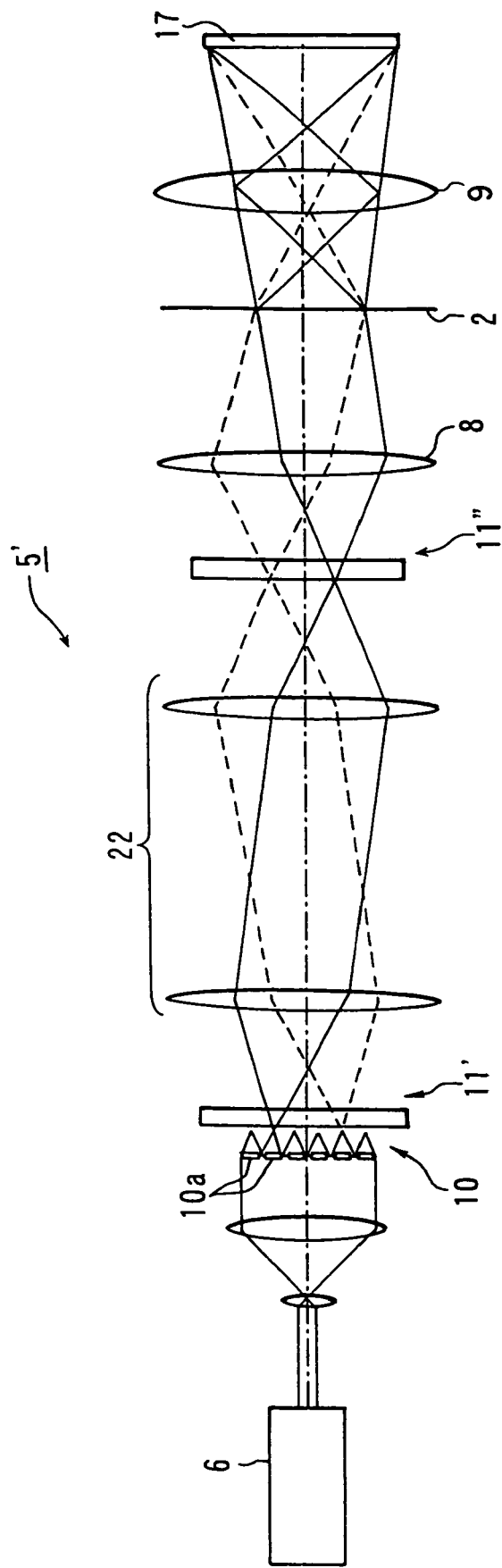
FIG. 7 is a schematic illustration of a second embodiment.

The second embodiment according to the present invention will be explained with reference to FIG. 7 as follows. The present embodiment illustrates another form of the smoothing optical system shown in FIG. 1. Therefore, other parts are omitted in FIG. 7 and the same elements as in the first embodiment have the same reference numbers. And the explanation of the other elements is also omitted.

A smoothing optical system 5' has a fly eye lens 10, the first phase shift plate 11' positioned on the secondary light source image side of this fly eye lens 10, a relay optical system 22, and the second phase shift plate 11". The second phase shift plate 11" and the first phase shift plate 11' sandwich the relay optical system 22, and the plate 11" is at the conjugate position from the plate 11' relative to the relay optical system 22.

As the first and second phase shift plates 11' and 11", the same plate as in the first embodiment may be used. The rotation direction of the phase rotating plate 11' and 11" should be the same because the image of the light source is reversed by the relay optical system 22.

This embodiment also makes it possible to change interference fringes and smooth the brightness of the laser beam in the same method as in the first embodiment because the laser beam passes through the fly eye lens 10 to make the intensity distribution of the laser beam source uniform and subsequently the laser beam passes through the first and second phase shift plates 11' and 11".

In this embodiment, the total of the rotation frequencies of the first and second phase shift plates 11' and 11" may be the same rotation frequency as that of the phase shift plate 11 in the first embodiment. As a result, the respective rotation frequencies of the plates 11' and 11" can be made lower, thereby lightening the burden for the apparatus.

It is important for this embodiment that the rotation frequencies of the first and second phase rotating plates 11' and 11" and the rotation frequency caused by the difference between them are not make identical to the frequency of the proper vibration frequency of this apparatus.

Third Embodiment

The third embodiment of the present invention will be described, with reference to FIGS. 8 to 14, in the following.

This embodiment illustrates still another example of the smoothing optical system in the first embodiment. Therefore, other parts are omitted in FIG. 8.

It is assumed that a linear polarized laser beam is emitted from a laser source 6 and the diameter of the laser beam is 2 L.

Figure 9:
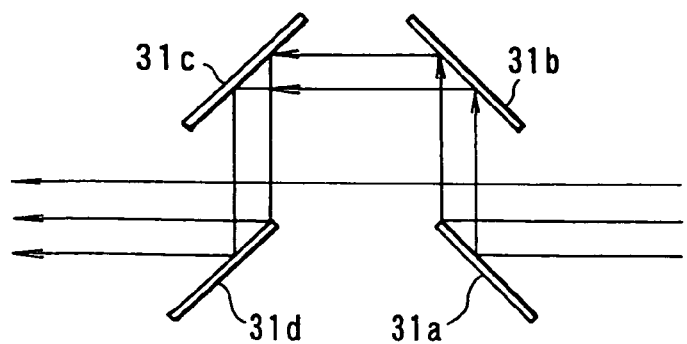
FIG. 9 is a schematic illustration of the third embodiment and shows a first laser beam dividing unit.

This laser beam is projected into the beam dividing unit 31. As shown in FIG. 9, the unit 31 divides the laser beam into an upper part and a lower part and passes the upper part therethrough. And the unit 31 detours the lower laser beam by reflecting it on mirrors 31a, 31b, 31c, and 31d inclined at 45 degrees against the lower ray bundle. Also, the path length of the detoured laser beam is set so that it will be longer than the non-detoured path length plus the coherency distance of the laser. At the front of the mirror 31d, the upper and lower laser beams are combined.

Figure 8:
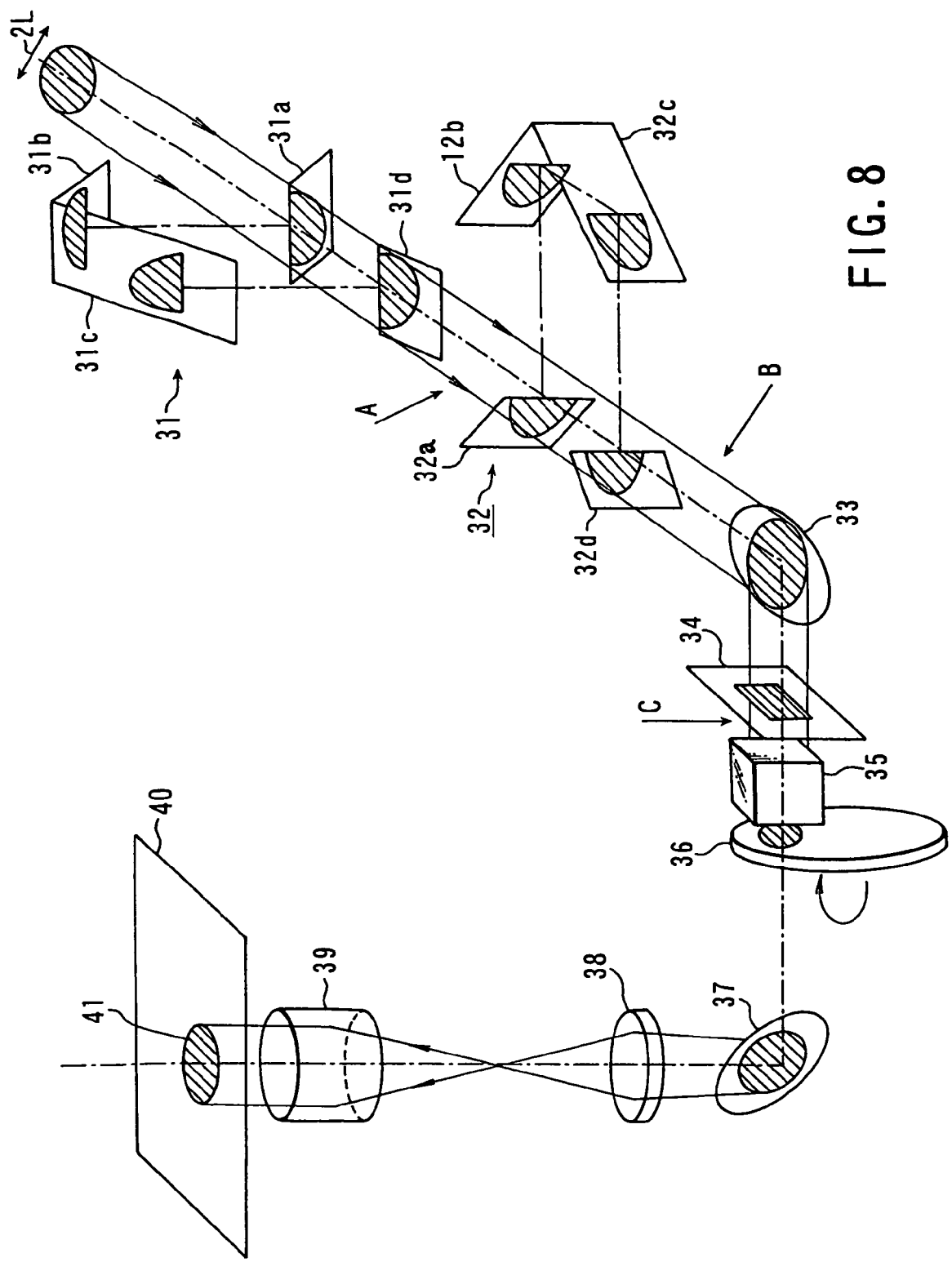
FIG. 8 is a schematic illustration of a third embodiment.
Figure 11:
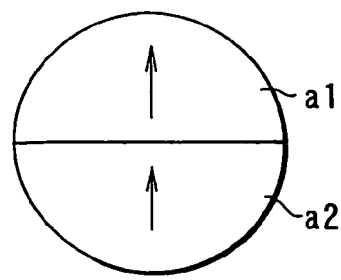
FIG. 11 is an illustration of the third embodiment showing the polarized direction of the laser beam after the first laser beam dividing unit.

This laser beam dividing unit 31 divides the laser beam into the upper and lower parts at the position A in FIG. 8 of the mirror 31d, illustrated in FIG. 11.

Figure 10:
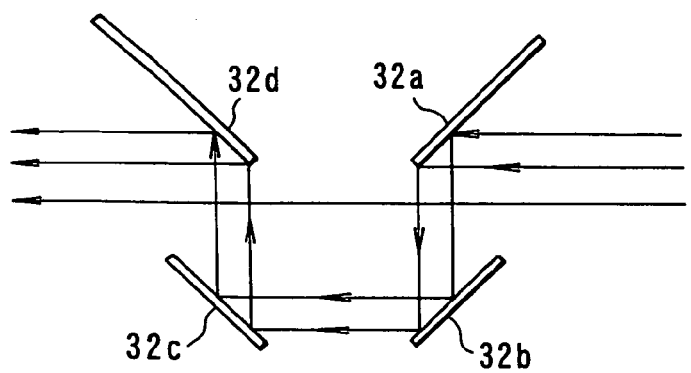
FIG. 10 is a schematic illustration of the third embodiment and shows a second laser beam dividing unit.

The second laser beam dividing unit 32 is provided at the downstream position of the beam dividing unit 31. As shown in FIG. 10, the unit 32 divides the incident laser beam into a right part and a left part and passes the left laser beam as it is therethrough. And the unit 32 detours the right laser beam by reflecting it on mirrors 32a, 32b, 32c, and 32d inclined at 45 degrees against the right laser beam. Also, the path length of the detoured laser beam is set so that it will be longer than the non-detoured path length plus the coherency distance of the laser.

Figure 12:
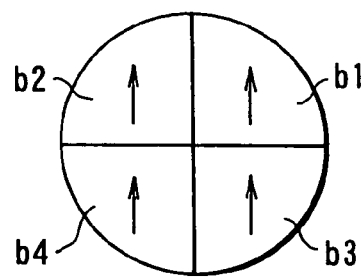
FIG. 12 is an illustration of the third embodiment showing the polarized direction of the laser beam after the second laser beam dividing unit.

The laser beam which has passed through the first and second beam dividing units 30 and 31 as above is divided into four portions b1-b4, which do not interfere with each other above, below, right, and left, as shown in FIG. 12, at the downstream position B (see FIG. 1) of the mirror 32d.

A reflecting mirror 33 is provided at the down-stream of the beam dividing unit 32. The reflecting mirror 33 bends the laser beam 90 degrees.

The laser beam reflected by the reflecting mirror 33 is projected into a half wave plate 34 which rotates the polarized direction of a part of the laser beam 90 degrees.

Figure 13:
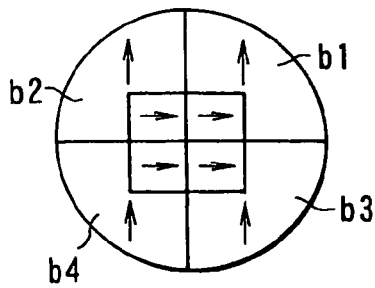
FIG. 13 is an illustration of the third embodiment showing the polarized direction of the laser beam of which polarization is partly rotated.

Accordingly, the polarized direction of the laser beam which has passed through this half wave plate 34 is as illustrated in FIG. 13.

A fly eye lens 35, downstream of the half wave plate 34, removes the interference effect of the laser beam.

A phase rotating plate 36 is downstream of the fly array lens 35. A motor(not shown) rotates the phase rotating plate 35. The phase rotating plate 36 has the same structure as in the first embodiment and a function of changing interference fringes of the laser beam.

The laser beam which has passed through the phase rotating plate 36 is bent 90 degrees by a reflecting mirror 37.

The laser beam reflected from the reflecting mirror 37 is condensed by a condenser lens 38 and concentrated on an object lens 39. Furthermore, the beam is concentrated by the object lens 10 to form a spot 41 on a mask-pattern 40.

In this structure, the coherency of the laser beam can be decreased by detouring a part of the laser beam so as to make the light paths different or rotating a part of the laser beam. Furthermore, passing this resultant laser through the phase rotating plate produces a uniform the brightness. Thus, substantially the same advantages as obtained by the first embodiment can be obtained.

This structure also permits the laser beam to be divided into four ray beams which do not interfere with each other by only 8 mirrors, so as to improve structural efficiency and light-transmitting efficiency.

Figure 14:
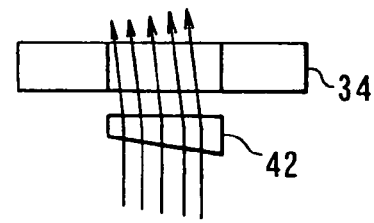
FIG. 14 is a schematic illustration showing a modification of the third embodiment.

If a prism 42 with a wedge form, as shown in FIG. 14, is arranged in the front of the half wave plate 34 shown in FIG. 8, speckles can be further decreased.

This prism 42 of a wedge form may be arranged not in the front of the half wave plate 34 but in the rear of it.

The invention described above makes it possible to solve the problem which occurs when a laser beam is adopted as a light source of an apparatus for inspecting a pattern defect and to examine the pattern defect with a higher resolving power so as to repair the defect of a minute mask-pattern.

Fourth Embodiment

The fourth embodiment according to the present invention will be explained with reference to FIGS. 15 to 17.

This embodiment relates to another example of the inspecting apparatus shown in FIG. 1, using the TDI sensor 17. With respect to the fourth embodiment, structural elements identical to those in FIG. 1 will be denoted by the same reference numerals, and their detailed explanations will be omitted. Furthermore, the fourth to sixth embodiments include methods and apparatuses obtained by combining the first to third embodiments.

The apparatus according to the fourth embodiment is provided to correct the variation of the amplitude of an output signal which occurs when the line width of the sample or photomask 2 varies, and thus prevent an error of determination with respect to whether or not the sample or photomask 2 is defective.

Another object of the apparatus is to prevent an error of determination whether or not the sample or photomask 2 is defective, when an error occurs in the speed of the XY table during measurement.

Figure 15:
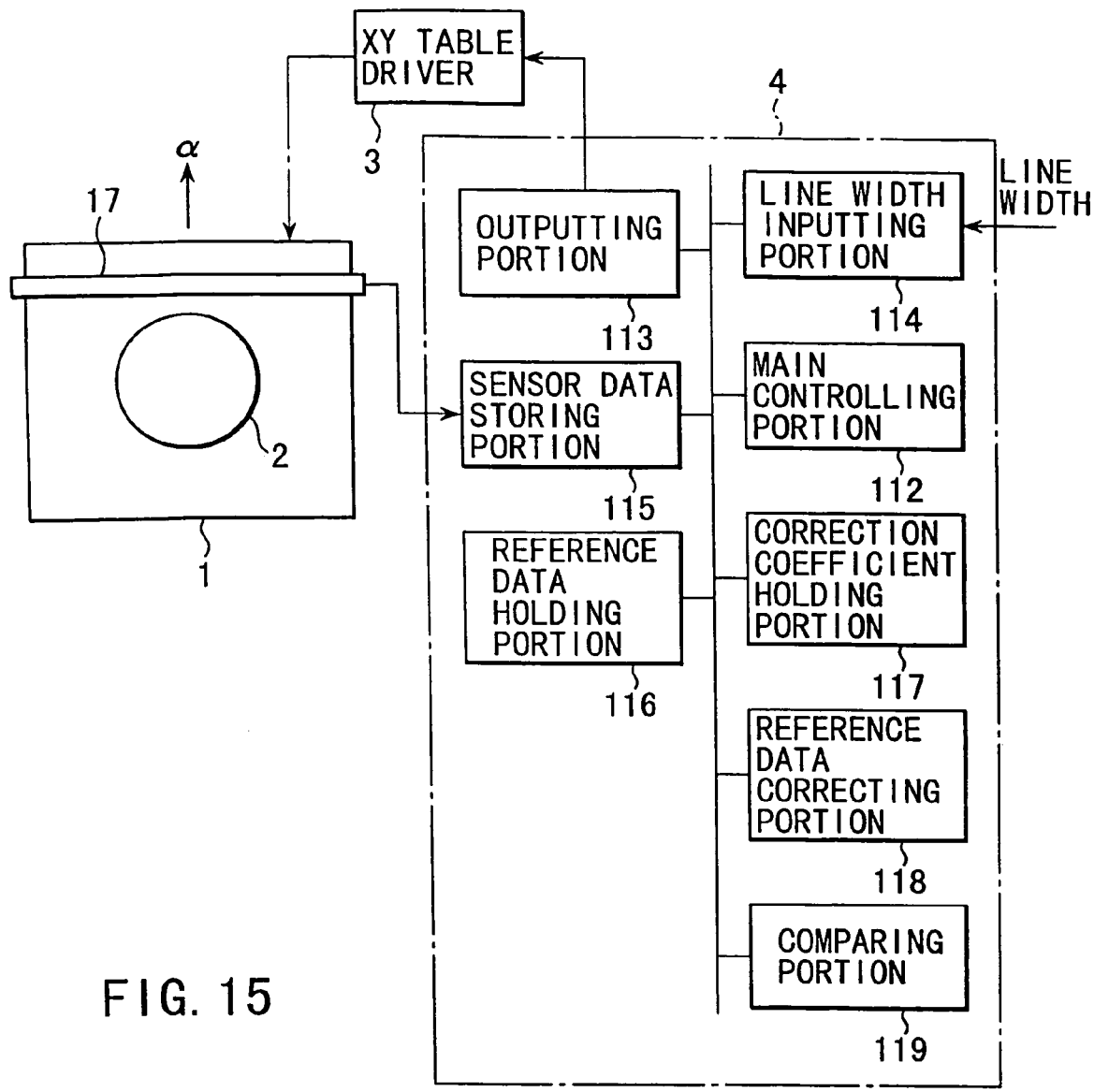
FIG. 15 is a schematic illustration of the fourth embodiment.
Figure 16:
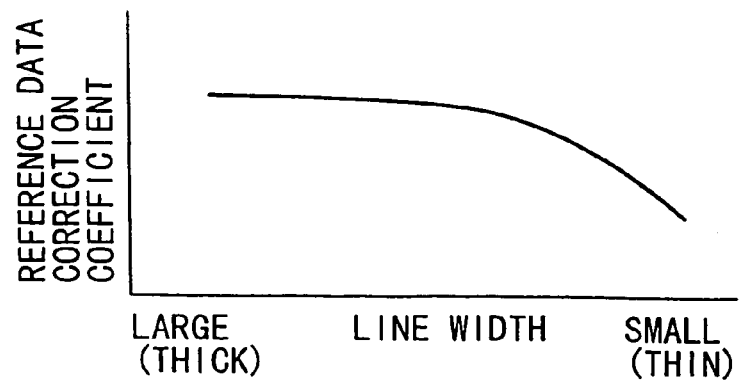
FIG. 16 is a view for illustrating correction coefficients and reference data.

FIG. 15 is a block diagram of the inspecting apparatus using the TDI sensor 17, Reference to FIG. 15, the TDI sensor 17 comprises only one line sensor. However, FIG. 15 shows this as a matter of convenience. Actually, the TDI sensor 17 has the same structure as that of the first embodiment, which comprises a plurality of line sensors.

The sample or photomask 2, e.g., a semiconductor wafer, is provided on the XY table 1, and the XY table 1 is moved by the driver 3 in a direction indicated by an arrow α.

On the other hand, the central controlling portion 4 receives an image signal output from the TDI sensor 17, and compares with the image signal with reference data, to thereby inspect the pattern of the sample or photomask 2. Whereas a main controlling portion 112 comprises a CPU, etc., the central controlling portion 4 comprises an outputting portion 113, a line width inputting portion 114, a sensor data storing portion 115, and a reference data holding portion 116, all connected to each other. Furthermore, the central controlling portion 4 includes a reference data correcting portion 118 and a comparing portion 119, which operate in response to a command given by the main controlling portion 112.

The outputting portion 113 has a function of transmitting a movement command generated from the main controlling portion 112. The line width inputting portion 114 is one of various kinds of inputting devices such as a keyboard and a mouse, and fetches line width data of the mask pattern formed on the sample or photomask 2.

The sensor data storing portion 115 serves to store the image signal output by the TDI sensor 17. The reference data holding portion 116 holds reference data (design patterns) which is used as comparison data when the sample or photomask 2 is inspected.

The correction coefficient holding portion 117 holds correction coefficients for use in correcting the amplitude of the image signal with respect to the line width of the mask pattern of the sample or photomask 2. The correction coefficient is applied to an image signal representing the mask pattern of the sample or photomask 2, when the image signal is compared with the reference data.

The correction coefficient is determined as follows:

First of all, a couple of samples or photomasks 2 each of them having a known mask pattern are prepared. It is moved in such a manner as to be scanned by the TDI sensor 17. Then, the maximum and minimum values of the output signal of the TDI sensor 17 are measured. The amplitude of the image signal is calculated from the measured maximum and minimum values, the amplitude changes corresponding to the variation of the line width of the mask pattern of the sample or photomask 2, which is measured by use of the TDI sensor 17.

Next, correction coefficients for use in making the reference data corresponding to each line width of the mask patterns coincide with the image signal output by the TDI sensor 17 are determined by use of the above amplitude and maximum and minimum values. Then, they are tabled. FIG. 16 shows the relationship between the line width and the correction coefficient of the reference data. As shown in FIG. 16, the smaller the line width, the smaller the correction coefficient.

The reference data correcting portion 118 receives line width data of the sample or photomask 2 which is fetched by the line width inputting portion 114, and reads out a correction coefficient corresponding to the received line width data, from the correction coefficient holding portion 117. Then, with respect to the line width, the reference data correcting portion 118 corrects in real time the reference data which is successively read out while the XY table 1 is being moved, by use of the read-out correction coefficient.

The comparing portion 119 compares the image signal of the TDI sensor 17 with the reference data corrected by the reference data correcting portion 118, to thereby inspect the sample or photomask 2.

Next, the inspecting operation of the apparatus having the above structure will be explained as follows:

When a sample or photomask 2 such as a semiconductor wafer is determined, the line width data of the sample or photomask 2 is input from the line width inputting portion 114. The line width data is sent to the reference data correcting portion 118 in response to the command from the main controlling portion 112.

When the sample or photomask 2 is placed on the XY table 1, and the driver 3 is operated in response to the command from the main controlling portion 112, the XY table 1 is moved in the direction indicated by the arrow α, with the sample or photomask 2 provided on the XY table 1.

At this time, the TDI sensor 17 receives light from the sample or photomask 2 on the XY table 1 at regular intervals while the sample or photomask 2 thereon is being moved, and successively accumulates signals representing the intensities of the light from the sample or photomask 2. The signals accumulated by the TDI sensor 17 are successively output therefrom and stored as data in the sensor data storing portion 115.

The comparing portion 119 receives the signals successively output from respective line sensors of the TDI sensor 17, and successively reads out and develops reference data from the reference data holding portion 116 while the XY table 1 is being moved. Then, the comparing portion 119 successively compares the above output signals of the TDI sensor 17 and the reference data.

Figure 17:
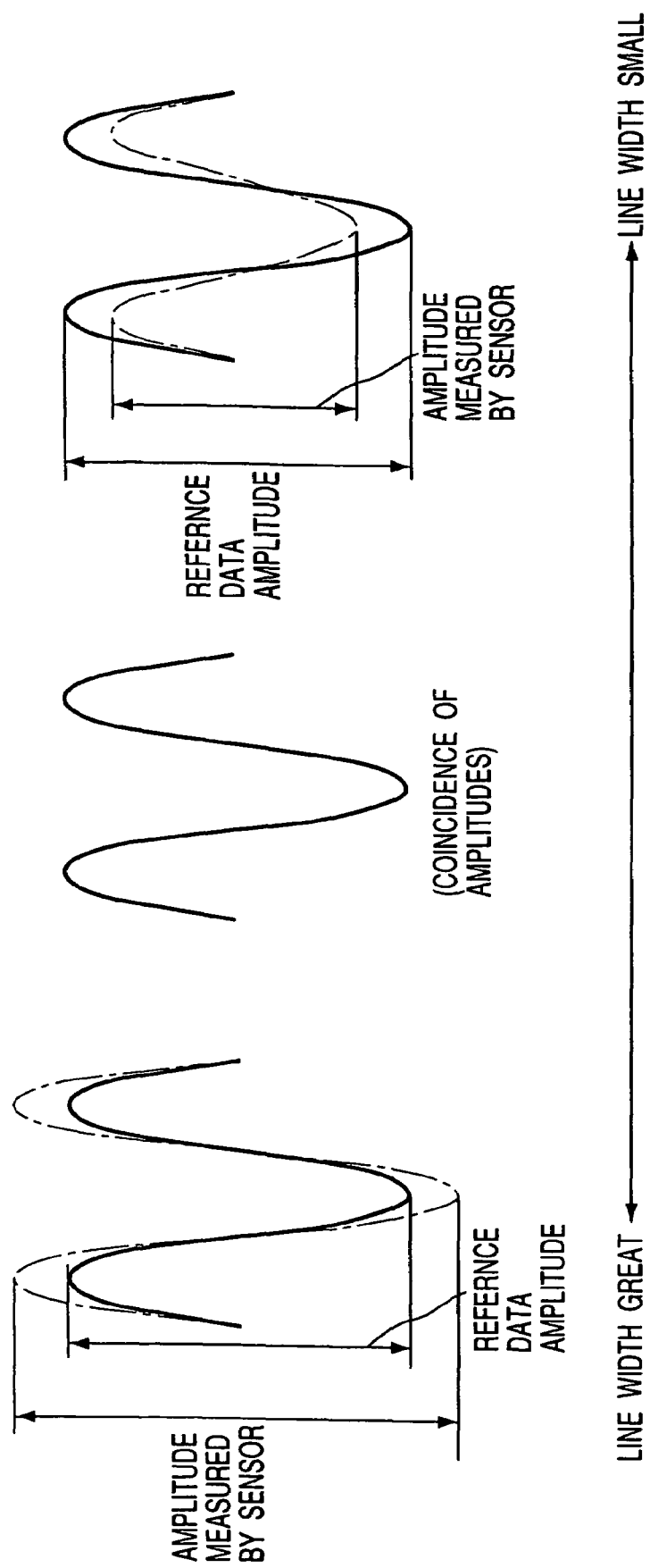
FIG. 17 shows a state wherein the amplitude of an output signal of a Time Delay Integration (TDI) sensor coincides with the amplitude of reference data after the amplitude of the reference data is corrected.

FIG. 17 illustrates that inconsistency of the output signal of the TDI sensor 17 and the reference data which occurs in the cases where the line width of the sample or photomask 2 is great, and where it is small. As shown in FIG. 17, when the line width of the sample or photomask 2 is equal to a predetermined line width, the amplitude of the output signal of the TDI sensor 17 coincides with the amplitude of the reference data. However, when the line width of the sample or photomask 2 is greater than the predetermined line width, the amplitude of the output signal of the TDI sensor 17 is greater than the amplitude of the reference data. In contrast, when the line width of the sample or photomask 2 is smaller than the predetermined line width, the amplitude of the output signal of the TDI sensor 17 is smaller than that of the reference data. In such a case, even when the mask pattern of the sample or photomask 2 coincides with the mask pattern represented by the reference data, there is a possibility that the sample or photomask 2 may be regarded as a defective one, This is because the amplitude of the output signal of the TDI sensor 17 does not coincide with that of the reference data.

In view of the above, according to the present invention, when the comparing portion 119 performs the above-mentioned comparing operation, the reference data correcting portion 118 receives the line width data of the sample or photomask 2 which is fetched by the line width inputting portion 114, reads out a correction coefficient corresponding to the received line width data from the correction coefficient holding portion 117, and corrects the amplitude of the reference data, which varies in accordance with the moved position of the XY table 1, by using the read-out correction coefficient.

The comparing portion 119 compares the output signal of the TDI sensor 17 and the reference data corrected by the reference data correcting portion 118. Then, it determines that the sample or photomask 2 is non-defective, when the amplitude of the output signal of the TDI sensor 17 coincides with that of the reference data, and determines that the sample or photomask 2 is defective, when the amplitude of the output signal of the TDI sensor 17 does not coincide with that of the reference data.

By virtue of such a structure, even if the line width of the sample or photomask 2 varies, and in particular, even if it varies slightly, the amplitudes of the output signals of the TDI sensor 17 do not coincide with that of the reference data. Thus, the apparatus does not make an error in determination on whether or not the sample or photomask 2 is defective. Therefore, it can inspect the sample or photomask 2 with high accuracy.

Fifth Embodiment

Next, the fifth embodiment will be explained with reference to FIG. 18. With reference to the fifth embodiment, structural elements identical to those in FIG. 15 will be denoted by the same reference numerals, and their detailed explanations will be omitted.

Figure 18:
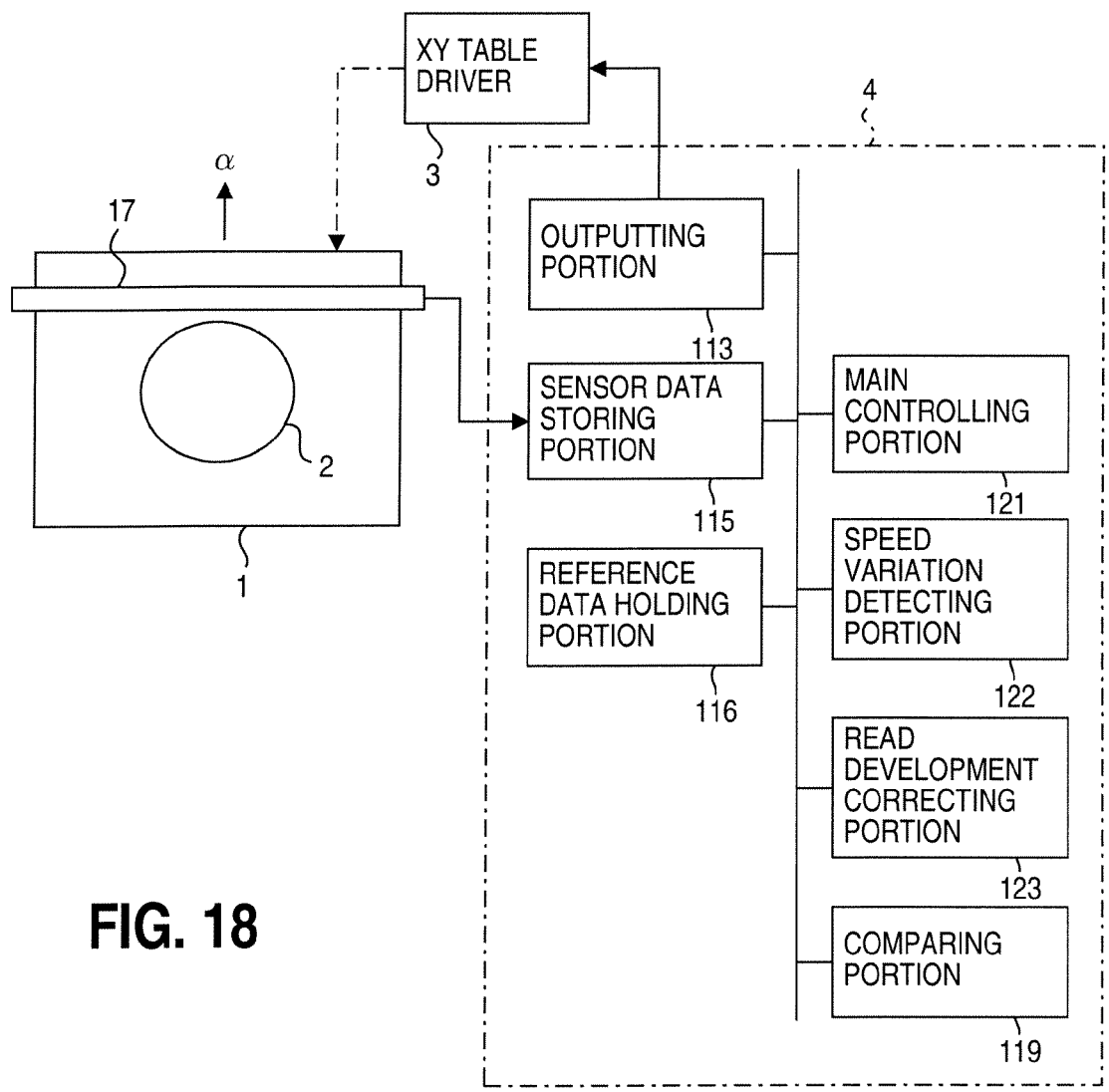
FIG. 18 is a schematic illustration of the fifth embodiment.

FIG. 18 is a block diagram of an inspecting apparatus according to the fifth embodiment.

According to this embodiment, the central controlling portion 4 fetches the output signal of the TDI sensor 17, and compares the output signal with the reference data, to thereby inspect the pattern of the sample or photomask 2. The central controlling portion 4 includes a speed variation detecting portion 122 and a read development correcting portion 123, which operate in response to a command given by a main controlling portion 121 comprising a CPU, etc.

The speed variation detecting portion 122 detects the variation of the relative speed of the sample or photomask 2 to the TDI sensor 17, i.e., the variation of the speed of the XY table 1. To be more specific, it compares the average speed of the XY table 1 moved before a lapse of a predetermined time period, with the present speed of the XY table 1, to thereby detect the variation of the speed of the XY table 1.

The read development correcting portion 123 corrects the timing at which the reference data is read out and developed from the reference data holding portion 116, in accordance with the variation of the speed of the XY table 1 which is detected by the speed variation detecting portion 122. To be more specific, the read development correcting portion 123 corrects the above timing such that the reference data is read and developed at an earlier timing, when the speed of the XY table 1 is high, and corrects the timing such that the reference data is read out and developed at a later timing, when the speed of the XY table 1 is low.

The inspecting operation of the apparatus having the above structure will be explained.

When the sample or photomask 2 is placed on the XY table 1, and the driver 3 is operated in response to a command from the main controlling portion 121, the XY table 1 is moved in a direction indicated by an arrow α, with the sample or photomask 2 provided on the XY table 1.

At this time, while the sample or photomask 2 is being moved, the TDI sensor 17 receives light intensities, from the sample or photomask 2 on the XY table 1, and accumulates those intensities as signals. Then, the TDI sensor 17 successively outputs the accumulates signals from its line sensors, respectively. The output signals of the TDI sensor 17 are successively stored as data in the sensor data storing portion 115.

Figure 19:
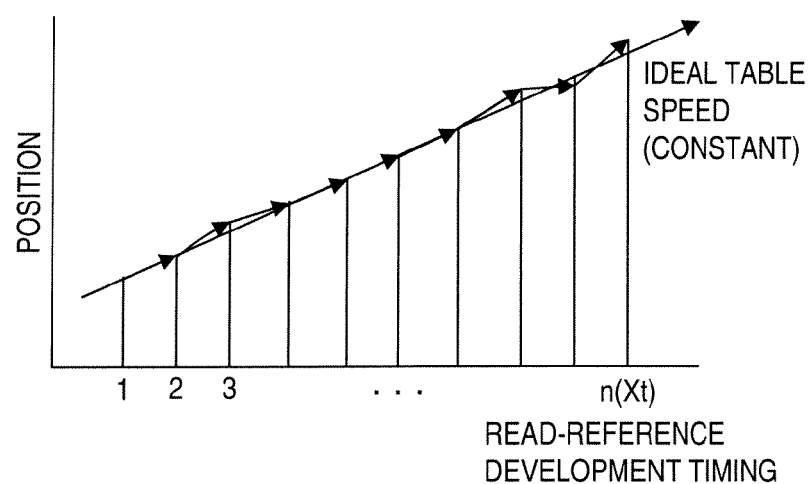
FIG. 19 is a view for showing an ideal speed of an XY table, and illustrating the variation of the speed of the XY table with inclined arrows.

The speed variation detecting portion 122 fetches an (n−1) number of data respectively representing the past speeds of the XY table 1 which have been detected before a predetermined time period lapses, and determines the average speed of the XY table 1 from the (n−1) number of data. Then, the speed variation detecting portion 122 compares the average speed with the reference data to detect the variation of the speed. FIG. 19 shows an ideal speed of the XY table 1, and illustrates the variation of the speed of the XY table 1 with inclined arrows.

The read development correcting portion 123 corrects the timing at which the reference data is read and developed from the reference data holding portion 116, in accordance with the variation of the speed which is detected by the speed variation detecting portion 122. For example, the read development correcting portions 123 corrects the above timing such that the reference data is read and developed at an earlier timing, when the speed of the XY table 1 is high, and corrects the timing such that the reference data is read and developed at a later timing, when the speed of the XY table 1 is low.

By virtue of the above feature, even if the speed of the XY table 1 varies, the positions thereof represented by the signals respectively output from the line sensors of the TDI sensor 17 coincide with the positions represented by the reference data which is successively read and developed.

The comparing portion 119 compares the signals which are successively output from the line sensors of the TDI sensor 17, respectively, with the reference data the read and development timing of which is corrected, at which the reference data is read and developed from the reference data holding portion 116. The comparing portion 119 determines that the sample or photomask 2 is non-defective, when the speeds represented by the above signals coincide with the speeds represented by the reference data, and determines that the sample or photomask 2 is defective, when the former speeds do not coincide with the latter speeds.

In such a manner, according to the fifth embodiment, even if the speed of the XY table 1 varies, the positions represented by the reference data read and developed can be made to coincide with those represented by the signals successively output from the line sensors of the TDI sensor 17, and thus the sample or photomask 2 can be inspected with high accuracy. In particular, the inspecting apparatus according to the fifth embodiment overcomes the following disadvantage of conventional inspecting apparatuses:

If the pattern of the sample or photomask 2 has lines each of a large width, inspection of the sample or photomask 2 is not greatly influenced by the pattern. However, if the pattern has lines each of a small width, inspection of the sample or photomask 2 is influenced by the pattern.

Such a problem does nor arise in the apparatus according to the fifth embodiment. Thus, the apparatus can inspect the sample or photomask 2 with high accuracy.

Sixth Embodiment

The sixth embodiment will be explained with reference to FIG. 20. With respect to the sixth embodiment, structural elements identical those in FIGS. 15 and 18 will be denoted by the same reference numerals, and their explanations will be omitted.

Figure 20:
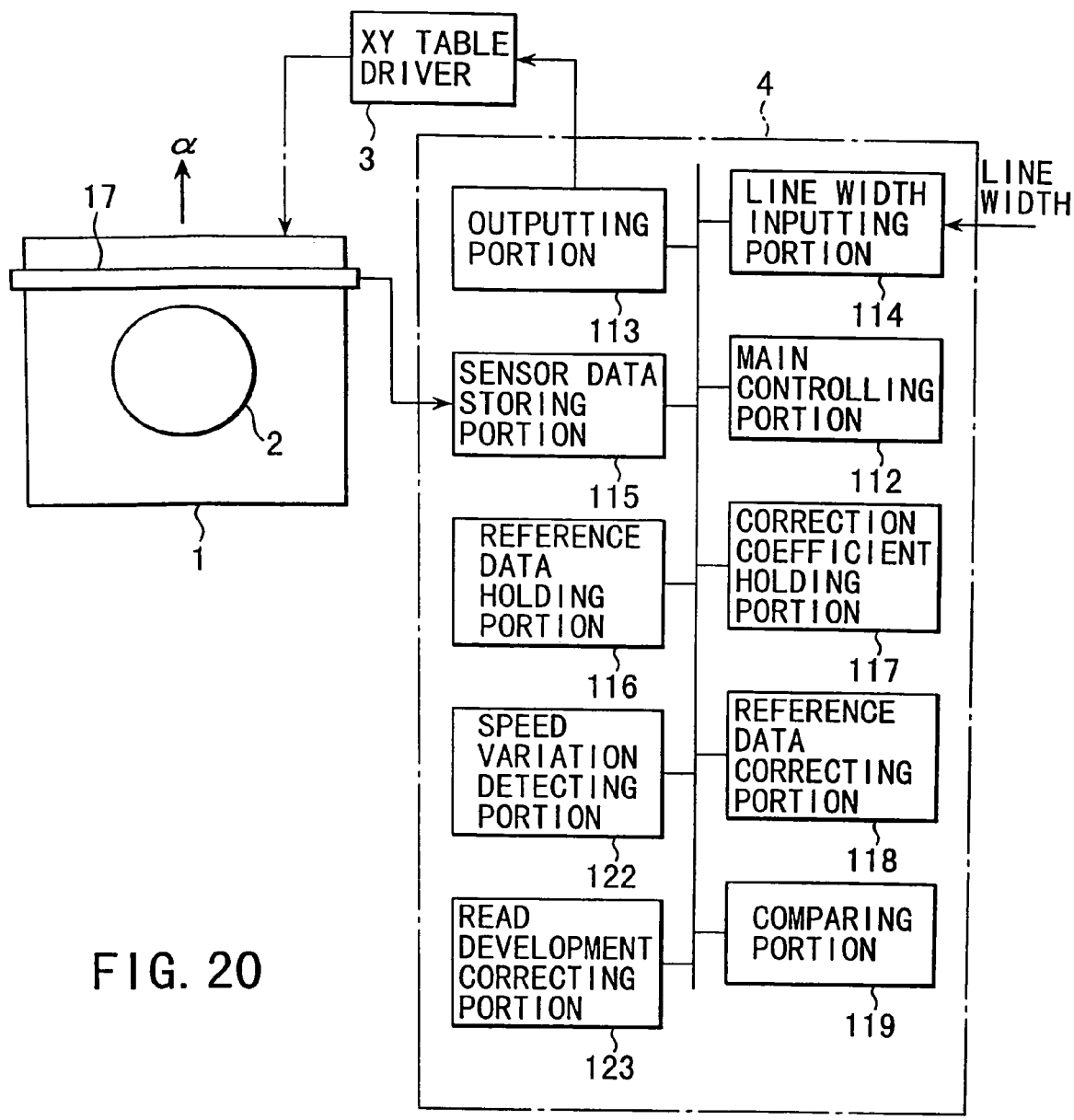
FIG. 20 is a schematic illustration of the sixth embodiment.

FIG. 20 is a block diagram of the inspecting apparatus having the TDI sensor 17. The inspecting apparatus is a combination of the apparatuses according to the fourth and fifth embodiments.

By virtue of such a structure (the above combination), the line width data of the sample or photomask 2 is input from the line width inputting portion 114, and sent to the reference data correcting portion 118 in response to the command of the main controlling portion 112.

When the sample or photomask 2 is placed on the XY table 1, and the XY table 1 is moved in a direction indicated by an arrow α, the TDI sensor 17 receives light from the sample or photomask 2, and accumulates signals representing the intensities of the light. Then, the line sensors of the TDI sensor 17 successively outputs the accumulated signals, respectively. Those output signals are successively stored as data in the sensor data storing portion 115.

The speed variation detecting portion 122 determines the average speed of the XY table 1 moved before a predetermined time period lapses, and compares the average speed and the present speed of the XY table 1 to detect the variation of the speed.

The read development correcting portion 123 corrects the timing at which the reference data is read and developed from the reference data holding portion 116, in accordance with the detected variation of the speed.

The reference data correcting portion 118 receives the line width data of the sample or photomask 2 which is fetched by the line width inputting portion 114, and reads out the correction coefficient corresponding to the received line width data, from the correction coefficient holding portion 117. Then, the reference data correcting portion 118 corrects in real time the amplitude of the reference data read and developed by the read development correcting portion 123 by use of the read-out correction coefficient.

The comparing portion 119 compares the signals successively output from the respective line sensors of the TDI sensor 17 with the reference data which is read out from the reference data holding portion 116, and the amplitude of which is corrected by the reference data correcting portion 118. The comparing portion 119 determines that the sample or photomask 2 is non-defective, when the output signals of the TDI sensor coincide with the reference data, and determines that the sample or photomask 2 is defective, when the output signals do not coincide with reference data.

In such a manner, according to the sixth embodiment, even if the line width of the sample or photomask 2 varies, and in particular, the line width varies slightly, the output signals do not coincide with the reference data with respect to the amplitude. Thus, the apparatus does not make an error of determination with respect to whether or not the sample or photomask 2 is defective. Furthermore, even if the speed of the XY table 1 varies, the positions of the reference data which is read and developed in accordance with the speed of the XY table 1 can be made to coincide with the positions of the signals successively output from the respective line sensors of the TDI sensor 17. Therefore, inspection of the sample or photomask 2 can be performed with high accuracy.

Seventh Embodiment

The inspection apparatus according to the seventh embodiment will be explained with reference to FIG. 20. With respect to the seventh embodiment, structural elements identical those shown in FIG. 1 will be denoted by the same reference numerals, and their explanations will be omitted.

The inspection apparatus of the seventh embodiment is featured in that its inspection means is made of a sensor 200 other than a TDI sensor. The sensor 200 is, for example, a camera-type sensor wherein elements are arranged in two dimensions, as in a CCD camera. Alternatively, a CCD line sensor having elements arranged in one dimension may be additionally employed. The camera-type sensor and the CCD line sensor have a signal accumulation function. During the accumulation of signals, interference patterns are changing constantly, and signals representing the interference patterns are averaged to obtain a pattern image free of interference noise.

When the camera-type sensor and the CCD line sensor are employed as sensors 200, signals representing constantly-changing interference patterns are averaged. By this averaging operation, interference noise is removed from a pattern image to be obtained.

The structure of the seventh embodiment enables formation of a photomask or sample image that is not adversely affected by the coherence of a laser beam. The photomask or sample image ensures highly reliable inspection. In addition, a defect of a photomask or sample can be repaired, referring to highly-reliable defect information.

Point-type sensors, such as a photodiode (PD) and a photomal (PMT), may be employed. When sensors of this type are used, the inspection optical system may be the same as that used when the TDI sensor is used. The point-type sensors are non-accumulation type sensors, and when they are used, signals representing constantly-changing interference patterns are averaged to obtain a pattern image free of interference noise.

As described above, the sensors applicable to the inspection apparatus of the present invention are not limited to TDI sensors; they may be a camera-type sensor, a CCD line sensor, a photodiode, a photomal, etc.

Eighth Embodiment

Figure 21:
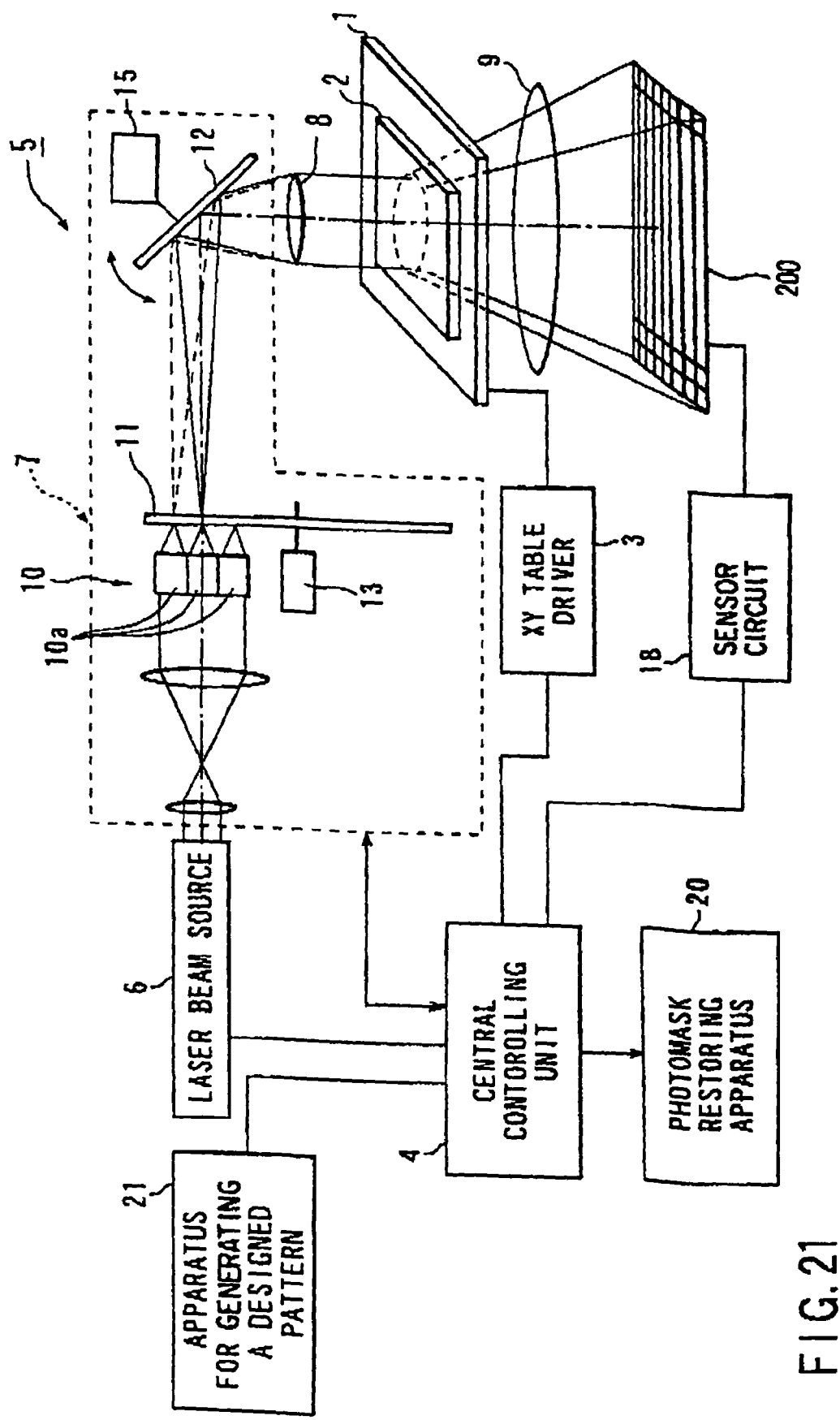
FIG. 21 is a schematic illustration of the seventh embodiment.
Figure 22:
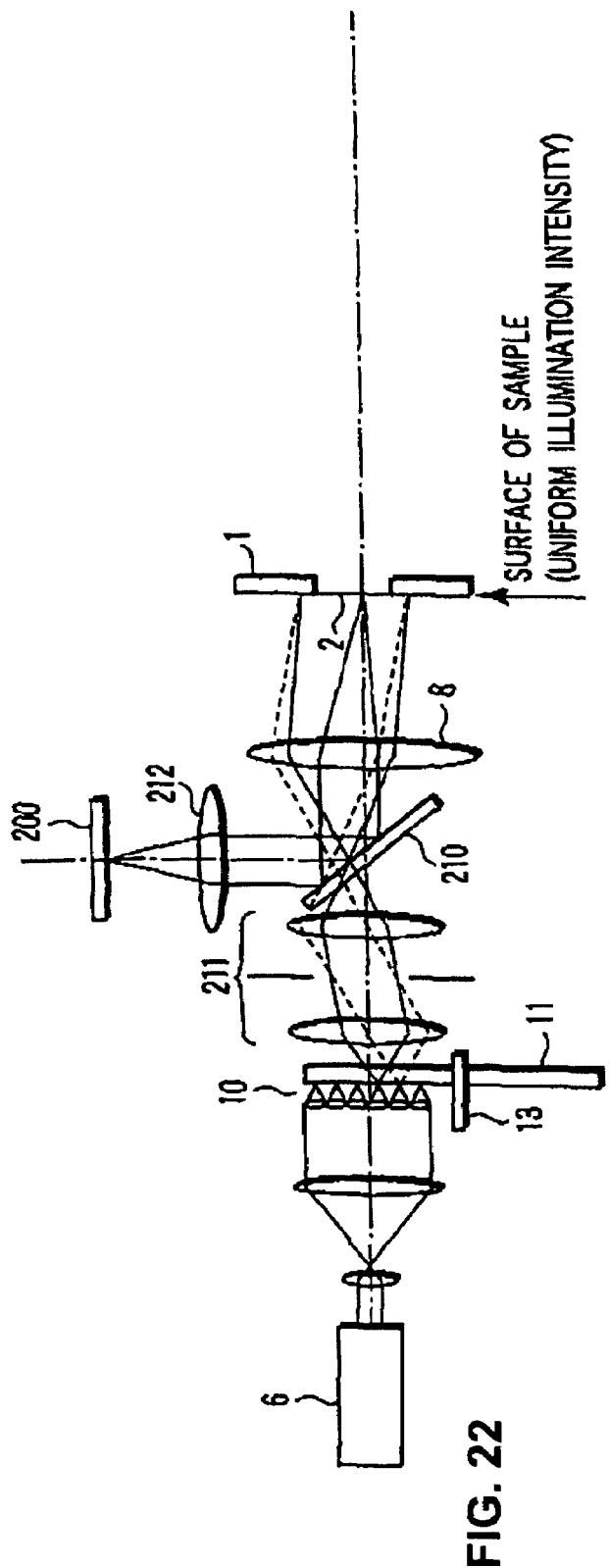
FIG. 22 is a schematic illustration of the eighth embodiment.

The inspection apparatus according to the eighth embodiment will be explained with reference to FIG. 22. With respect to the eighth embodiment, structural elements identical those shown in FIGS. 1 and 21 will be denoted by the same reference numerals, and their explanations will be omitted.

The eighth embodiment is an embodiment wherein a sample other than a photomask or sample is inspected. The sample may be a wafer, a liquid crystal panel, an element-mounted board, or the like. Since these samples do not allow transmission of light, a reflection-type optical system is used for the inspection. That is, light reflected by the surface of a sample is reflected in such a manner that the reflected light travels in a direction perpendicular to the optical path of illuminating light. The reflected light enters a focusing lens 212, by which it is made to fall on a sensor 200. In FIG. 22, reference numeral 211 denotes a relay lens system.

As described above, the sample inspected by the inspection apparatus is not limited to a photomask or sample; it may be a wafer, a liquid crystal panel, an element-mounted board, or the like.

Ninth Embodiment

Figure 23:
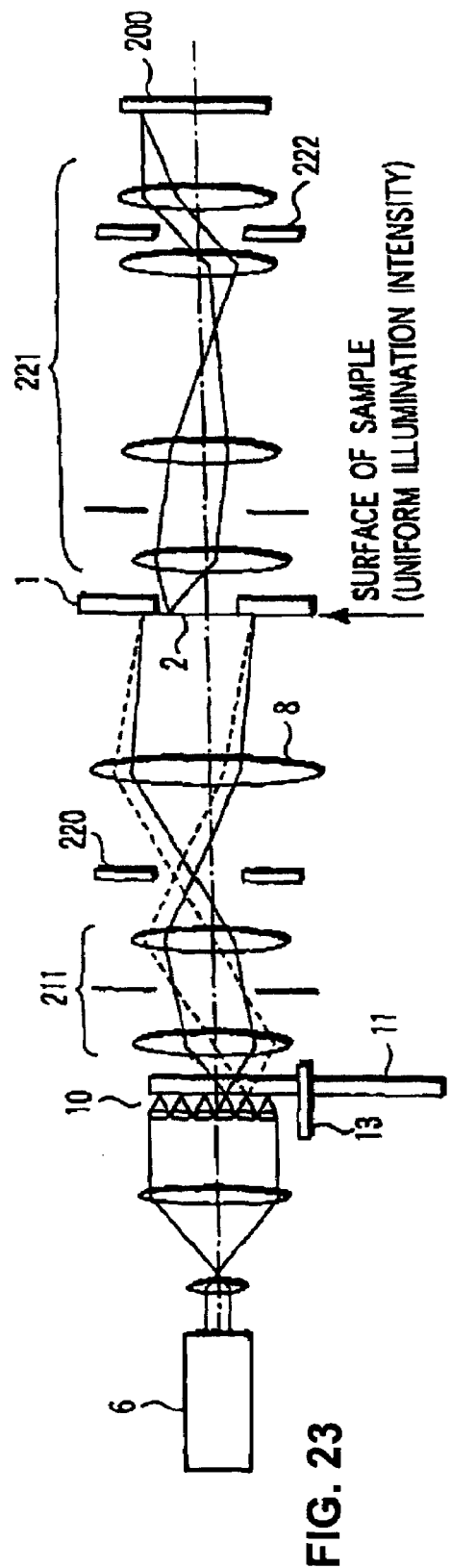
FIG. 23 is a schematic illustration of the ninth embodiment.

The inspection apparatus according to the ninth embodiment will be explained with reference to FIG. 23. With respect to the ninth embodiment, structural elements identical those shown in FIGS. 1, 21 and 22 will be denoted by the same reference numerals, and their explanations will be omitted.

According to the ninth embodiment, the illuminating optical system, by which a sample is illuminated, employs an illuminating-system pupil filter 220. The characteristics of this illuminating-system pupil filter 220 can be determined in a desirable manner. For example, the shape a light beam has after transmission, transmittance distribution, phase, etc. can be adjusted. In addition, the focusing system employs a power-variable lens assembly 221. Owing to the use of these, a sample pattern can be projected on the sensor under a desired magnification.

The power-variable lens assembly 221 can employ a focusing-system pupil filter 222. The characteristics of this focusing-system pupil filter 222 can be determined in a desirable manner as above. By properly adjusting the characteristics of the illuminating-system pupil filter 220 and the focusing-system pupil filter 222, a pattern image can be adjusted in characteristics. The characteristics of the illuminating-system pupil filter 220 and the focusing-system pupil filter 222 can be so determined as to emphasize a pattern defect.

The present invention includes a semiconductor device manufactured by use of a photomask or sample inspected, repaired and formed according to the first to sixth embodiments, and a method for manufacturing the semiconductor device by use of the photomask or sample.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for manufacturing a semiconductor device by using a photomask after inspecting the photomask, comprising:

generating a laser beam;

changing a phase of the laser beam to smooth a brightness distribution of the laser beam;

applying the smoothed laser beam to the photomask;

acquiring an image of the photomask using a sensor while the laser beam and the photomask are relatively moved;

examining the image of the photomask for a defect of a mask pattern of the photomask; and manufacturing a semiconductor device by using the photomask after the examining the image of the photomask.

2. The method of claim 1, wherein a signal integration time of the sensor is enough for smoothing the brightness distribution of the laser beam in the step of changing.

3. The method of claim 1, wherein the laser beam used in the generating is a source which can continuously or intermittently emit a laser beam.

4. The method of claim 1, wherein the changing includes changing an optical axis of the laser beam against a sample continuously or intermittently to change interference fringes of the laser beam thereby smoothing the brightness distribution of the laser beam.

5. The method of claim 4, wherein a period when the optical axis of the laser beam is changed against the sample is decided in accordance with a signal integration time of the sensor.

6. The method of claim 1, wherein the changing includes passing the laser beam into a rotating phase shift plate which has different thickness points, to change the phase of the laser beam, thereby smoothing the brightness distribution of the laser beam.

7. The method of claim 6, wherein the rotation velocity of the phase shift plate is enough for signal integration of the sensor.

8. The method of claim 6, wherein the changing includes passing the laser beam into a plurality of rotating phase shift plates.

9. The method of claim 8, wherein a total rotation rate of the phase shift plates is enough for smoothing the brightness for signal integration of the sensor.

10. The method of claim 1, wherein the changing includes a first step of detouring a part of the laser beam and a second step of detouring the part of the laser beam detoured in the first detouring step, in a different direction from the detour of the first detouring step; thereby dividing the laser beam to reduce a coherency of the laser beam and smooth the brightness distribution of the laser beam.

11. The method of claim 1, wherein the changing includes a first step of detouring about one-half of the laser beam, and a second step of detouring the half of the laser beam detoured in the first detouring step, in a direction inclined at 90 degrees against the detour direction in the first detouring step; thereby dividing the laser beam into four beams which do not interfere with each other, to reduce a coherency of the laser beam and make uniform the brightness distribution of the laser beam.

12. The method of claim 10, wherein a path length difference between a total path length in the first detouring step and in the second detouring step and a path length of the laser beam not detoured is a coherency distance or more, thereby dividing the laser beam into four ray beams which do not interfere with each other.

13. The method of claim 10, further including providing a half wave plate for rotating, at 90 degrees, a polarized direction of a part of the laser beam, the part including a center of the laser beam, among the laser beams which have been detoured via the second detour step.

14. The method of claim 13, further including providing a prism with a wedge form in front or in rear of the half wave plate.

15. The method of claim 1, further including outputting an image signal output from the sensor after correcting the image signal by use of a correction coefficient associated with a line width of a pattern of a sample.

16. The method of claim 1, wherein in the examining, a signal output from the sensor is compared with reference data which is read, to thereby detect whether or not the mask pattern has a defect.

17. The method of claim 16, further including detecting a relative speed of a sample to the sensor, and correcting timing at which the reference data is read, in accordance with the relative speed.

18. A method for manufacturing a semiconductor device by using a photomask after manufacturing the photomask, comprising:
forming a pattern onto the photomask;
generating a laser beam;
changing a phase of the laser beam to smooth the brightness distribution of the laser beam, and applying the smoothed laser beam to the photomask;
acquiring an image of the photomask with a sensor as the laser beam and the photomask are relatively moved;
acquiring a defect of a mask pattern of the photomask on the basis of the image of the photomask;
when the defect of the mask pattern is detected, specifying a position of the defect of the mask pattern, and repairing the defect of the mask pattern; and
manufacturing a semiconductor device by using the photomask after the repairing the defect of the mask pattern.

19. The method of claim 18, wherein a signal integration time of the sensor is enough for smoothing the brightness distribution of the laser beam in the changing.

20. The method of claim 18, wherein a laser beam source used in the generating is a source which can continuously or intermittently emit the laser beam.

21. The method of claim 18, wherein the changing includes changing an optical axis of the laser beam against the photomask continuously or intermittently to change interference fringes of the laser beam, thereby smoothing the brightness distribution of the laser beam.

22. The method of claim 21, wherein a period when the optical axis of the laser beam is changed against the photomask is decided in accordance with a signal integration time of the sensor.

23. The method of claim 18, wherein the changing includes passing the laser beam into a rotating phase shift plate which has different thickness points, to change a phase of the laser beam, thereby smoothing the brightness distribution of the laser beam.

24. The method of claim 23, wherein a rotation velocity of the phase shift plate is enough for signal integration of the sensor.

25. The method of claim 23, wherein the changing includes passing the laser beam into a plurality of rotating phase shift plates.

26. The method of claim 25, wherein a total rotation rate of the phase shift plates is enough for smoothing the brightness distribution for signal integration of the sensor.

27. The method of claim 18, wherein the changing includes a first step of detouring a part of the laser beam, and a second step of detouring the part of the laser beam detoured in the first detouring step, in a different direction from the detour of the first detouring step; thereby dividing the laser beam to reduce a coherency of the laser beam and smooth the brightness distribution of the laser beam.

28. The method of claim 18, wherein the changing includes a first step of detouring about one-half of the laser beam, and a second step of detouring the half of the laser beam detoured in the first detouring step, in a direction inclined at 90 degrees against the detour direction in the first detouring step; thereby dividing the laser beam into four beams which do not interfere with each other, to reduce a coherency of the laser beam and make uniform the brightness distribution of the laser beam.

29. The method of claim 27, wherein a path length difference between a total path length in the first detouring step and in the second detouring step and a path length of the laser beam not detoured is a coherency distance or more, thereby dividing the laser beam into four ray beams which do not interfere with each other.

30. The method of claim 27, further including providing a half wave plate for rotating, at 90 degrees, a polarized direction of a part of the laser beam, the part including a center of the laser beam, among the laser beams which have been detoured via the second detouring step.

31. The method of claim 30, further including providing a prism with a wedge form in front or in rear of the half wave plate.

32. The method of claim 18, further including outputting an image signal output from the sensor after correcting the image signal by use of a correction coefficient associated with a line width of the mask pattern of the photomask.

33. The method of claim 18, wherein in the detecting, an image signal output from the sensor is compared with reference data which is read out, to thereby detect whether or not the mask pattern has a defect.

34. The method of claim 33, further including detecting a relative speed of the photomask to the sensor, and correcting timing at which the reference data is read out, in accordance with the relative speed.

* * * * *